United States Patent [19]

Corrin

[11] Plant 4,873

[45] Aug. 10, 1982

[54] GRAPE VINE

[76] Inventor: Allan A. Corrin, 6541 S. Holbrook, Reedley, Calif. 93654

[21] Appl. No.: 216,062

[22] Filed: Dec. 12, 1980

[51] Int. Cl.[3] ..... A01H 5/03

[52] U.S. Cl. ..... Plt./47

[58] Field of Search ..... Plt./47

*Primary Examiner*—Robert E. Bagwill

*Attorney, Agent, or Firm*—Huebner & Worrel

[57] ABSTRACT

A grape vine which bears fruit resembling that of the Thompson Seedless grape vine (unpatented), which it most nearly resembles, but distinguished by bearing berries of large size in shatter-resistant bunches without girdling the vines or the application of gibberellin, by superior storing and shipping characteristics, and by maturing about 30 days later than fruit of the Thompson Seedless variety.

1 Drawing Figure

BACKGROUND OF THE NEW VARIETY

The well-known Thompson Seedless or Sultanina variety (unpatented) of grape vine is one of the most extensively planted varieties, its fruit being used for raisins and wine, as well as being a leading table grape. Despite its widespread popularity for table use, the Thompson Seedless grapes have numerous deficiencies for such use. The skin of the grapes of this variety are relatively tender for table grape use and thus are easily damaged in shipment and storage. The skin of grapes of this variety begin to acquire an unattractive brownish color after being in cold storage for 45 to 60 days. The grapes do not attain a large and attractive size unless the vines are girdled or have a growth regulator, such as gibberellin, applied at the proper time during the growing season. At the present time, therefore, table grapes of the Thompson Seedless variety are almost universally from vines which have been girdled or sprayed with gibberellin. A further disadvantage of the Thompson Seedless variety of grapes for table use is that bunches of grapes tend to shatter, particularly when the vines are not girdled or sprayed with a growth regulator.

As with other fruits, a variety of grape vine bearing fruit which ripens substantially earlier or later than the usual variety having the same general characteristics is highly advantageous in that fruit of the earlier or later ripening variety can be marketed at a relatively high price due to the then existing scarcity of other satisfactory fruit of the same type. In many cases, difference of a week in ripening date can contribute significantly to the commercial success of a new variety. In particular, it has been recognized that a variety of grape vine bearing fruit similar to that of the Thompson Seedless, but ripening substantially later, would be highly advantageous. The advantage of such a variety would, of course, be significantly enhanced if the effective length of its harvest season were also extended by superior cold storage characteristics and the ability to remain on the vine for a significant period without deterioration.

ORIGIN AND ASEXUAL REPRODUCTION OF THE NEW VARIETY

The new variety of grape vine was discovered by me in 1975 as a seedling on my farm near the intersection of Frankwood and Goodfellow Avenues near the City of Reedley, in the County of Fresno, in the State of California.

For many years, I have cross-pollinated grape blossoms, or had them cross-pollinated, obtained the resultant seeds, and grown seedlings produced from such seeds all in a vineyard on my designated farm with a view toward developing improved varieties of grape vines. The subject variety of grape vine originated as a seedling from cross-pollination between grape vine varieties on my farm; however, the records of the parent grape vines involved in such cross-pollination and the resulting seedlings were inadvertently destroyed in 1963 and the parental source of the new variety is unknown.

The new variety was asexually reproduced by me by rooting cuttings thereof in 1978 on my farm, and the fruit and vine characteristics resulting from the cuttings proved identical to those of the original seedling.

SUMMARY OF THE NEW VARIETY

The instant variety of grape vine is generally characterized by its bearing of light greenish grapes, normally referred to as "white", having elongated, elliptical grapes resembling berries borne by the Thompson Seedless (unpatented) variety of grape vine when the latter variety is girdled and/or treated with a growth regulator such as gibberellin.

The new variety is distinguished from the Thompson Seedless variety in a number of advantageous respects. Grapes borne thereby ripen about 30 days later, from Sept. 10 to Oct. 1 under the growing conditions on the above-designated farm, than the fruit of the Thompson Seedless variety. The effective harvest season of the new variety is extended beyond the harvest season for the Thompson Seedless variety, not only by the later ripening of fruit from the new variety, but because fruit of the new variety will hang on the vine with virtually no deterioration in some instances until frost, until Nov. 15 on the above-designated farm. The effective marketing season of the new variety is further substantially extended by the superior keeping characteristics of its grapes after harvest, grapes of the new variety remaining in cold storage up to 90 or more days without browning while, as before stated, that of the Thompson Seedless variety begins to turn brown in 45 to 60 days.

Another important and advantageous distinction of fruit of the new variety is that the skin of the grapes thereof is substantially tougher than the skin of the Thompson Seedless variety so that the new variety is not easily damaged in shipping or storage. Other distinctions of the new variety contributing to its superior shipping and storage characteristics are that the stems of the new variety are larger than those of the Thompson Seedless, the berries are more difficult to detach so that mature clusters of grapes do not shatter. While the skin toughness and resistance to shatter of Thompson Seedless grapes can be substantially improved by girdling or application of gibberellin, the superiority of the subject variety in shipping and storage characteristics is obtained without either girdling or such application. The new variety, without any such treatment, bears grapes superior in many characteristics to grapes borne by the Thompson Seedless variety which has been girdled or has had gibberellin applied.

Not only does the subject variety possess superior storage and shipping characteristics without treatment such as girdling or the application of a growth regulator, but individual berries of the new variety attain a size equal to that of the largest berries usually found in fruit of the Thompson Seedless variety with such treatment, this berry size of the new variety being attained without such treatment.

Another distinction of the subject variety is that its grapes are more thoroughly seedless than those of the Thompson Seedless variety.

The grapes of the subject variety are further distinguished from that of the Thompson Seedless in that the instant variety "sugars" later than the Thompson Seedless and the individual berries have ends which are substantially more blunt, berries of the new variety having almost flat or, at least, hemispherical ends. A final characteristic which clearly distinguishes the subject variety of grape vine from the Thompson Seedless variety is the form of the leaf at the petiole sinus. As is well known, the transversely opposite lobes of each leaf of the Thompson Seedless variety overlap to some extent centrally of this sinus. However, this sinus of many leaves of the new variety are fully open and the opposite lobes do not overlap.

BRIEF DESCRIPTION OF THE DRAWING

The accompanying drawing is a color photograph of a bunch of mature grapes borne by the subject variety of grape vine together with a pair of representative leaves and with two grapes which are disposed adjacent to a scale and are divided to show their flesh color and seedless configuration.

DETAILED DESCRIPTION

Referring more specifically to the pomological details of this new and distinct variety of grape vine, the following has been observed under the ecological conditions prevailing in the above-designated farm near Reedley, Calif. All color code plate identifications and color names in quotation marks are by reference to the Maerz and Paul *Dictionary of Color,* Second Edition, published in 1950 by the McGraw-Hill Book Company, Inc., other color names being common descriptive names.

VINE

*Size: Medium.*

Growth: Medium.

Productivity: Medium and regular.

Canes: Medium thickness with joints spaced an average distance and with tendrils of medium slenderness, length (25–30 cm), abundance, and strength.

Foliage: Leaves are average in number; have a length of 115 to 165 mm, average 140 mm, and a width of 130 to 145 mm, average 137.5 mm; the color of the leaves at time of harvest of the fruit being

*Upperside.*—Olive green (23 E 5) to (23 L 6).

*Lowerside.*—Yellow green (20 C 3) to (21 F 2).

Flowers: Average in number, similar in configuration and color to those of the Thompson Seedless variety (unpatented), and having a blooming season of 7 to 10 days in length.

FRUIT

Maturity: 30 days after the Thompson Seedless variety, Sept. 10 to Oct. 1 on the above-designated farm near Reedley, Calif., in 1980. The berries can remain on the vine until frost or until the middle of November.

Size: Large without girdling of vine or application of gibberellin or other growth regulator, typically attaining an average diameter of 20 mm and a length from base to apex of 28 mm; that is, as large as berries of the Thompson Seedless variety with such treatment.

Color: Similar to Thompson Seedless, a light yellow green with skin ranging from (19 H 2) to (20 I 4) and the flesh of a berry divided in a central longitudinal plane with the skin otherwise intact being (19 F 2).

Average number of bunches to vine: 25 to 40.

Average number of berries to bunch: 150 to 200.

Number of seeds to berry: Seedless, lesser trace of seed development than in Thompson Seedless variety.

Productivity: Average.

Skin: Tight, substantially more tough than Thompson Seedless.

Ripening: On the above-designated farm, harvest can begin about Sept. 15 and peak about Oct. 15.

Bunches ripen: Evenly.

Texture: Medium.

Flavor: Similar to Thompson Seedless.

Aroma: Similar to Thompson Seedless.

Eating quality: Similar to Thompson Seedless.

Juice quality: Similar to Thompson Seedless.

Shipping and storing quality: Substantially superior to Thompson Seedless due to tougher skin, heavier stems, and berries being more adherent thereto, these factors being naturally present without girdling of the vines or treatment with gibberellin or other growth regulator.

Uses: Primarily fresh table due to ripening date and storage and shipping characteristics, but also suitable for raisin or wine production.

Although the new variety of grape vine bears the described characteristics as a result of the growing conditions in Fresno County, Calif., in the central part of the San Joaquin Valley, it is to be understood that variations of the usual magnitude in characteristics incident to growing conditions, fertilization, pruning, and pest control are to be expected.

Having thus described and illustrated my new variety of grape vine, what is new and desired to be secured by Letters Patent is:

1. A new and distinct variety of grape vine, substantially as illustrated and described, characterized by its general resemblance to the Thompson Seedless grape vine (unpatented) in bearing elongated, seedless, light green berries, but being distinguished therefrom and characterized as to novelty by having leaves wherein the petiole sinus of each leaf is not closed by the adjacent lobes thereof and by bearing berries having a more blunt apical end; the fruit of the new variety, in comparison with fruit of the Thompson Seedless variety, maturing about 30 days later, retaining a desirable color in cold storage for a substantially longer period of time, having a tougher skin, and being superior in seedless quality, the clusters borne by the new variety being resistant to "shatter" and the berries thereof being of large size without girdling or application of gibberellin or other growth regulator, the shatter-resistance of the bunches and the size of the berries borne by the new variety without girdling or such application being equal to said bunch and berry characteristics of the Thompson Seedless variety with girdling and/or such application.

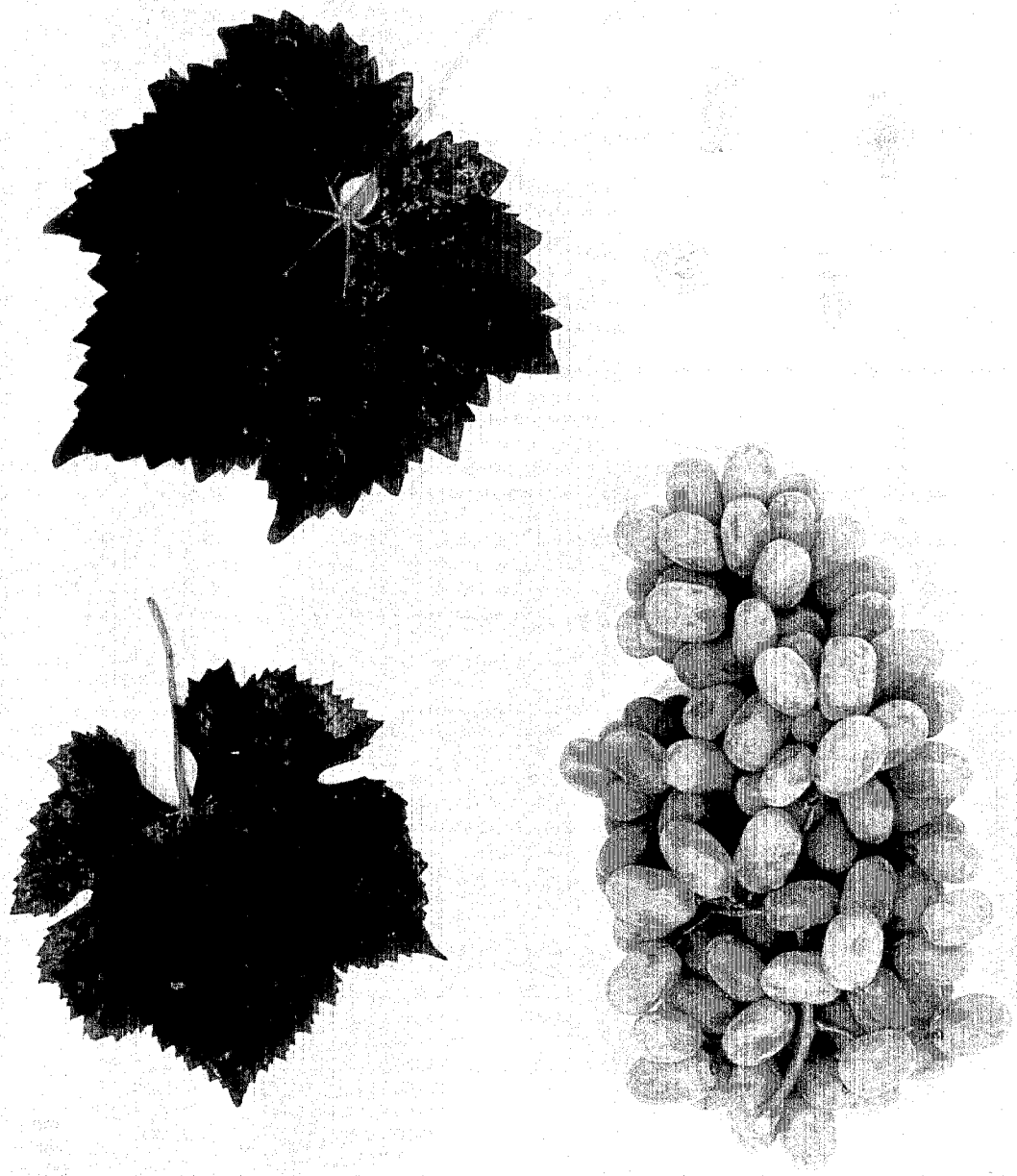

* * * * *